(12) United States Patent
van Arendonk

(10) Patent No.: US 10,456,098 B2
(45) Date of Patent: Oct. 29, 2019

(54) MAMMOGRAPHY DETECTOR WITH SMALL CHEST DISTANCE

(71) Applicant: Teledyne Digital Imaging, Inc., Waterloo (CA)

(72) Inventor: Anton Petrus Maria van Arendonk, Waterloo (CA)

(73) Assignee: TELEDYNE DIGITAL IMAGING, INC., Waterloo (CA)

( * ) Notice: Subject to any disclaimer, the term of this patent is extended or adjusted under 35 U.S.C. 154(b) by 51 days.

(21) Appl. No.: 15/525,166

(22) PCT Filed: Nov. 21, 2014

(86) PCT No.: PCT/CA2014/000844
§ 371 (c)(1),
(2) Date: May 8, 2017

(87) PCT Pub. No.: WO2016/077906
PCT Pub. Date: May 26, 2016

(65) Prior Publication Data
US 2017/0311912 A1    Nov. 2, 2017

(51) Int. Cl.
*A61B 6/00* (2006.01)
*G01T 1/20* (2006.01)
*H01L 27/146* (2006.01)

(52) U.S. Cl.
CPC .......... *A61B 6/4208* (2013.01); *A61B 6/4233* (2013.01); *A61B 6/502* (2013.01); *G01T 1/2018* (2013.01); *H01L 27/146* (2013.01)

(58) Field of Classification Search
None
See application file for complete search history.

(56) References Cited

U.S. PATENT DOCUMENTS

| | | | |
|---|---|---|---|
| 8,614,421 B2 | 12/2013 | van Arendonk et al. | |
| 2004/0155320 A1 | 8/2004 | DeJule et al. | |
| 2005/0254620 A1 | 11/2005 | Shoji et al. | |
| 2011/0113611 A1* | 5/2011 | Tonami | G01T 1/1644 |
| | | | 29/428 |
| 2013/0308755 A1* | 11/2013 | Ishida | G01T 1/202 |
| | | | 378/62 |
| 2014/0008749 A1 | 1/2014 | Nomura et al. | |
| 2014/0119503 A1 | 5/2014 | Matsuzawa | |
| 2014/0205060 A1 | 7/2014 | Kim et al. | |

(Continued)

FOREIGN PATENT DOCUMENTS

WO    WO 2016/011522 A1    1/2016

OTHER PUBLICATIONS

Extended European Search Report for European Application No. 14906646.6, dated Jun. 11, 2018.

(Continued)

*Primary Examiner* — Edwin C Gunberg
(74) *Attorney, Agent, or Firm* — K&L Gates LLP

(57) ABSTRACT

An X-ray detector is manufactured bonding detector layers onto a main frame leaving a protruding edge portion extending beyond edge of the detector layers. The protruding edge portion of the main frame is then detached from the main frame along a detachment line adjacent the edge of the detector layers before a cover with a thin edge wall is applied to the detector stack.

18 Claims, 3 Drawing Sheets

(56) References Cited

U.S. PATENT DOCUMENTS

2017/0131415 A1\* 5/2017 Van Arendonk ...... F16B 11/006

OTHER PUBLICATIONS

International Preliminary Report on Patentability for International Application No. PCT/CA2014/000844, dated May 23, 2017.
International Search Report for International Application No. PCT/CA2014/000844, dated Aug. 5, 2015.
Written Opinion of the International Searching Authority for International Application No. PCT/CA2014/000844, dated Aug. 5, 2015.

\* cited by examiner

MAMMOGRAPHY DETECTOR WITH SMALL CHEST DISTANCE

CROSS-REFERENCE TO RELATED APPLICATION

This application is a U.S. National Stage Entry under 35 U.S.C. § 371 of International Patent Application No. PCT/CA2014/000844, entitled MAMMOGRAPHY DETECTOR WITH SMALL CHEST DISTANCE, filed Nov. 21, 2014, the entire disclosure of which is hereby incorporated by reference herein.

FIELD OF THE INVENTION

This invention relates to the field of mammography, and in particular to a mammography detector.

BACKGROUND OF THE INVENTION

In mammography screening X-ray film has been replaced by digital detectors. A typical setup is shown in US patent publication No. 2014/0205060. The patient places her breasts on a horizontal plate containing the X-ray detector, which consists of an array of stacks of laminar components bonded together. The end wall of the detector is placed against the chest wall of the patient. In order to obtain as complete a reading as possible, it is important that the distance to the edge of the active portion of the detector be as small as possible so that as much of the patient's breast as possible lies over the active surface of the detector. It is also important to ensure that the detector can be manufactured economically using automated manufacturing techniques.

The laminar components are manufactured by bonding them as individual layers together on a supporting frame. The supporting frame must extend beyond the end wall of the stack in order to provide a trench to collect excess adhesive as described in our co-pending application no. PCT/CA2014/000584, which is hereby incorporated by reference. This tends to result in the active area of the detector being displaced from the chest, an effect that results in reducing the effectiveness of the detector.

SUMMARY OF THE INVENTION

According to the present invention there a method of making an X-ray detector comprising providing a main frame for supporting a detector stack, the main frame having a detachable protruding edge portion; bonding detector layers onto the main frame leaving the protruding edge portion extending beyond edge of the detector layers; detaching the protruding edge portion of the main frame along a detachment line adjacent the edge of the detector layers; and applying a cover with a thin edge wall to the detector stack.

Typically, the main frame is made of aluminum, although it can be made of other materials, such as other metals, plastic or reinforced plastic. The protruding edge portion of the main frame may be snapped off manually or automatically using robotic techniques. Alternatively, the protruding edge portion may be removably attached to the main frame, for example, with screws. To facilitate removal it may be made of, or coated with, a release agent, such as Teflon™.

In accordance with another aspect the invention an X-ray detector comprises a detector stack bonded onto a frame base portion of the main frame, an edge of said frame base portion being located such that it is aligned with, or underhangs an edge of said stack; and a protective cover with a thin edge wall applied to the detector stack.

Yet another aspect the invention provides a precursor assembly for making an X-ray detector, comprising a detector stack bonded onto a main frame, an edge of said main frame protruding beyond an edge of the detector stack, said protruding edge portion of the main frame being detachable along a line that is aligned with, or underhangs the edge of said detector stack.

BRIEF DESCRIPTION OF THE DRAWINGS

The invention will now be described in more detail, by way of example only, with reference to the accompanying drawings, in which.

DETAILED DESCRIPTION OF PREFERRED EMBODIMENTS

Figure 1:
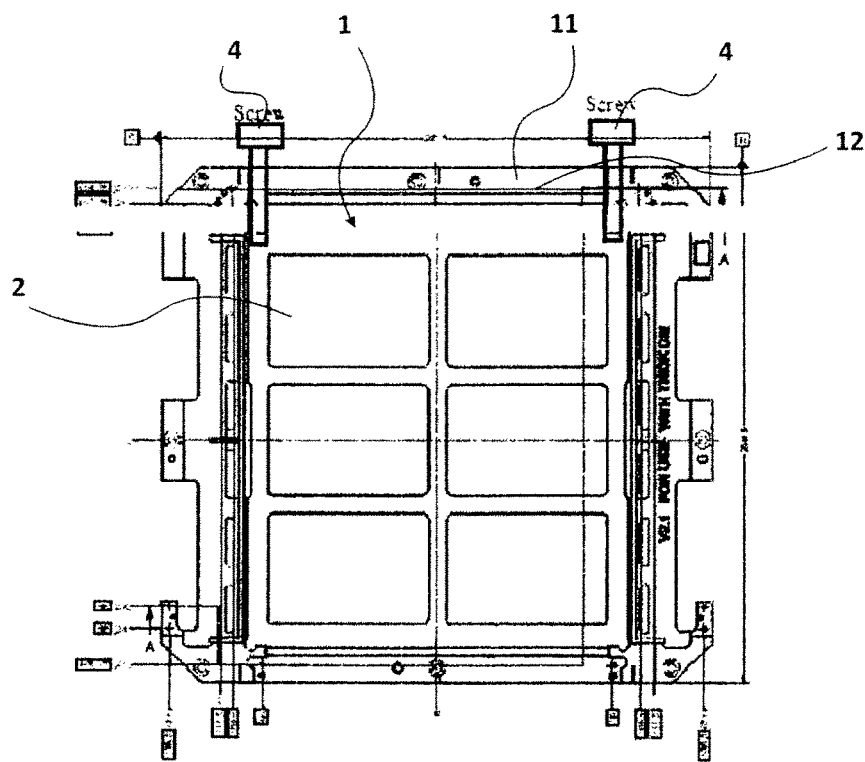
FIG. 1 is a plan view of a main frame.
Figure 2:
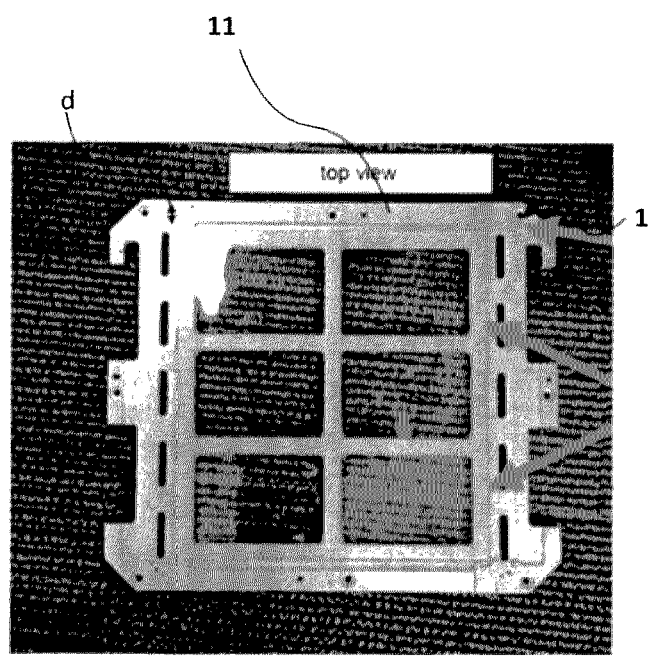
FIG. 2 is a photograph showing a plan view of the main frame with the glass carrier in place.
Figure 3:
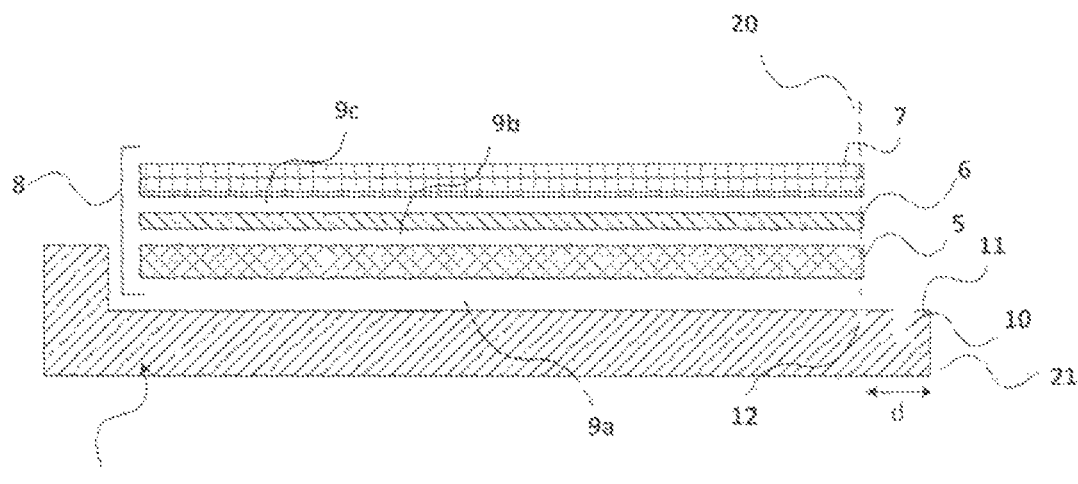
FIG. 3 is a cross section through a partly formed detector stack located on a main frame.

Referring now to FIGS. 1 to 3, an X-ray detector stack is manufactured by bonding an array of individual silicon tiles 6 onto a glass carrier 5.

The glass carrier 5 is located within a recess formed in a metal supporting main frame 1 containing rectangular openings or windows 2 to permit the passage of ultraviolet light to cure the adhesive for bonding the layers together. The main frame 1 is typically made of aluminum, but it can be made of other metals, or plastic or reinforced plastic.

During manufacture, as shown in FIGS. 2 and 3, first the glass carrier 5 is bonded to the main frame 1 (FIG. 2) with a suitable adhesive. The silicon tiles 6 are then bonded onto the glass carrier layer 5 in the form of an array, with the silicon tiles abutting each other.

Next the fiber optic plate (FOP) 7, which is coated on top with scintillator, such as Cesium Iodide (CsI), is bonded over all the tiles 6 and a protective foil (not shown) is laid on top of the scintillator coating on the fiber optic plate 7. The fiber optic plate 7 comprises a bundle of micron-sized optical fibers, and in effect serves as a medium to convey the light and image with high efficiency and low distortion to the silicon sensor. Unlike a normal optical lens, no focusing distance is required.

The layers 5, 6, and 7 are bonded together and onto the main frame 1 using a suitable adhesive 9a, 9b, 9c. The adhesive 9b between layers 5 and 6 can be cured by passing ultraviolet light through the windows 2.

The main frame 1 has a protruding edge portion 11 (FIG. 3). As described in our co-pending application referred to above, a trench 10 is provided in the protruding edge portion 11 of the main frame 1 between the edge 20 of the layers of the stacks and the edge 21 of the main frame 1 to catch excess adhesive 9a, 9b, and 9c flowing out from between the layers, 5, 6, and 7 in each of the stacks 8.

A problem arises in that the protruding portion 11 necessary to support the trench 10 inevitably extends the main frame 1 by an amount d beyond the edge 20 of the stack 8, as a result of which the edge 20 of the stack is displaced from the chest wall 18 (FIG. 4) when the detector is in use.

In accordance with embodiments of the invention a prescribed scribe line 12, forming a detachment line, is provided in the main frame 1 prior to placement of the layers of the detector stack 8. This can be scribed mechanically or by any suitable means. The scribe line 12 is located in alignment with, or slightly inwardly of (i.e. underhangs), the edge 20 of the layers of the stacks 8.

Figure 4:
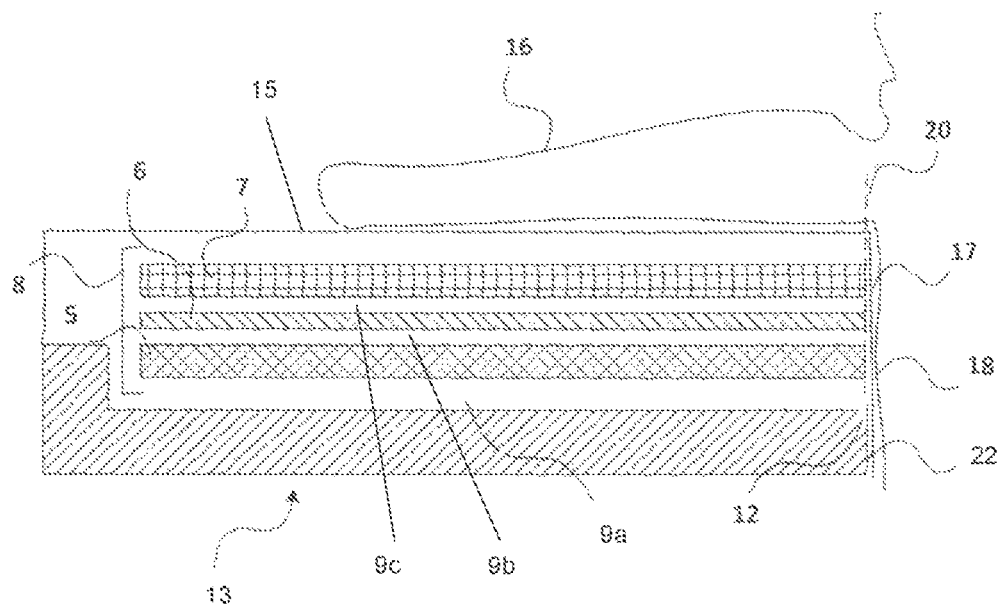
FIG. 4 is a cross section through a completed detector including a protective cover.
Figure 5:
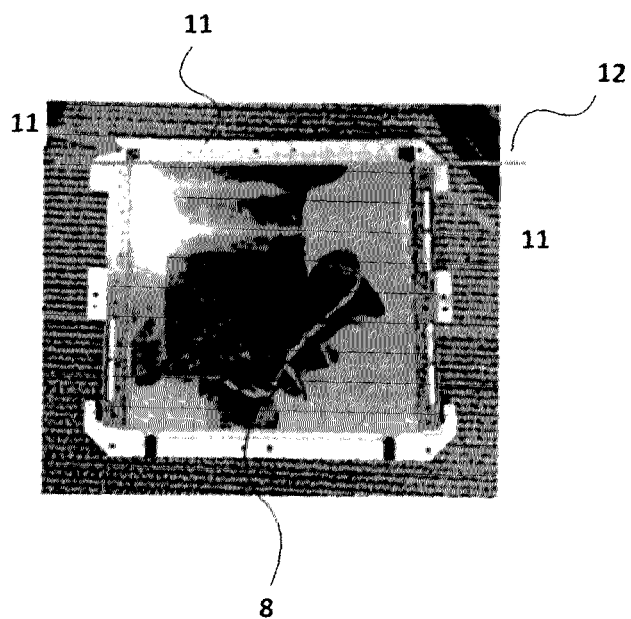
FIG. 5 shows a completed stack with silicon tiles in place.

After placement of the layers 5, 6, and 7, the protruding edge portion 11 of the main frame 1 is snapped off, either manually or using robotic techniques, so that the edges 20 of the stacks 8 align with the edge 22 of the frame base portion 13 of the main frame 1 as shown in FIG. 4. The protruding edge portion 11 is snapped off as one of the last stages in the manufacturing process. As a result the active components of the device are protected during handling.

A conventional carbon cover 15 is then placed over the detector. The cover can be held in place by screws or other fixing means, or could be molded in place. The wall 17 of the cover 15 can be made very thin, namely less than 1 mm, so that when the X-ray detector abuts the chest wall 18 with the breast 16 lying on the active surface of the detector, the distance between the active edge 20 of the stacks 8 and the chest wall is very small.

In an alternative embodiment, the protruding portion 11 can be provided as a separate piece that is screwed to the main frame 1 by means of screws 4 as shown in FIG. 1. In this case the piece can be made of, or coated with, Teflon/Delrin etc, to facilitate removal when the piece is removed. This acts as a release agent. After assembly of the detector stack, the screws 4 are removed, and the separate piece can be peeled away, facilitated by the action of the release agent. In this case the detachment line is provided by the interface between the removable piece and the main part of the frame 1.

The described technique is suitable for large-scale manufacturing.

The invention claimed is:

1. A method of making an X-ray detector, comprising:
   providing a main frame for supporting a detector stack, wherein the main frame comprises a detachable protruding edge portion;
   bonding detector layers onto the main frame leaving the protruding edge portion extending beyond an edge of the detector layers;
   detaching the protruding edge portion of the main frame along a detachment line adjacent the edge of the detector layers; and
   applying a cover with a thin edge wall to the detector stack;
   wherein a trench to collect excess adhesive is located in the protruding edge portion of the main frame.

2. The method of claim 1, wherein the detachment line is aligned with the edge of the detector layers.

3. The method of claim 1, wherein the detachment line is located slightly inwardly of the edge of the detector layers.

4. The method of claim 1, wherein the detachment line is defined by a scribe line that is pre-scribed into the main frame, and the protruding edge portion is snapped off along the scribe line after assembly of the detector stack.

5. The method of claim 1, wherein the protruding edge portion is removably attached to the main frame by fasteners.

6. The method of claim 5, wherein the fasteners are screws.

7. The method of claim 1, wherein the detector layers comprise a glass carrier plate bonded onto a frame base portion of the main frame, one or more silicon tile layers, and a fiber-optic plate coated with a scintillator material.

8. The method of claim 1, wherein the main frame is made of aluminum.

9. The method of claim 1, wherein the main frame further comprises a frame base portion, and wherein the detector layers are bonded to the frame base portion.

10. The method of claim 9, wherein the cover is applied to the edge of the detector layers and an edge of the frame base portion.

11. The method of claim 10, wherein the cover is less than 1 mm thick.

12. An X-ray detector, comprising:
    a detector stack bonded onto a frame base portion, an edge of the frame base portion being located such that it is aligned with, or under hangs an edge of the detector stack; and
    a protective cover with a thin edge wall applied to the edge of the detector stack,
    wherein the edge of the frame base portion further comprises a trench to collect excess adhesive flowing from the detector stack and
    wherein the trench is configured to be removed along a detachment line formed in the frame base portion.

13. The X-ray detector of claim 12, wherein the detector stack comprises a glass carrier plate bonded onto the frame base portion, one or more silicon tile layers, and a fiber-optic plate coated with a scintillator material.

14. The X-ray detector of claim 12, wherein the frame base portion is made of aluminum.

15. The X-ray detector of claim 12, wherein the protective cover is applied to the edge of the detector stack and the edge of the frame base portion.

16. A precursor assembly for making an X-ray detector, comprising:
    a detector stack bonded onto a main frame;
    a protruding edge portion comprising an edge of the main frame protruding beyond an edge of the detector stack;
    wherein the protruding edge portion is detachable along a line that is aligned with, or underhangs the edge of the detector stack; and
    wherein the protruding edge portion comprises a trench to collect any adhesive flowing from the detector stack.

17. The precursor assembly of claim 16, wherein the line is in the form of a scribe line pre-scribed into the main frame.

18. The precursor assembly of claim 16, wherein the protruding edge portion is detachably attached to the main frame with fasteners.

* * * * *